(12) United States Patent
Liu

(10) Patent No.: US 7,351,567 B2
(45) Date of Patent: Apr. 1, 2008

(54) ENZYMATIC RESOLUTION OF SELECTIVE ESTROGEN RECEPTOR MODULATORS

(75) Inventor: Kevin K. Liu, East Lyme, CT (US)

(73) Assignee: Pfizer Inc., New York, NY (US)

( * ) Notice: Subject to any disclaimer, the term of this patent is extended or adjusted under 35 U.S.C. 154(b) by 675 days.

(21) Appl. No.: 10/791,462

(22) Filed: Mar. 2, 2004

(65) Prior Publication Data

US 2004/0176415 A1     Sep. 9, 2004

Related U.S. Application Data

(62) Division of application No. 09/850,545, filed on May 7, 2001, now Pat. No. 6,828,134.

(60) Provisional application No. 60/202,418, filed on May 8, 2000.

(51) Int. Cl.
C12N 9/16      (2006.01)
A01N 43/54    (2006.01)
A61K 31/497  (2006.01)
A61K 31/517  (2006.01)

(52) U.S. Cl. .................. 435/196; 514/266; 514/256; 514/252.17

(58) Field of Classification Search ............. 435/196; 514/228.2, 233.5, 234.5
See application file for complete search history.

(56) References Cited

U.S. PATENT DOCUMENTS

| 4,808,605 A | 2/1989 | Branca et al. .............. 514/394 |
| 5,106,750 A | 4/1992 | Wong et al. ................. 435/280 |
| 5,248,609 A | 9/1993 | Petzoldt et al. ............. 435/280 |
| 5,552,412 A | 9/1996 | Cameron et al. ............ 514/317 |
| 5,714,642 A | 2/1998 | Didion et al. ............... 568/810 |
| 6,180,375 B1 | 1/2001 | Truesdell .................... 435/121 |

FOREIGN PATENT DOCUMENTS

| EP | 0357009 | 3/1990 |
| EP | 0989187 | 3/2000 |
| WO | WO 8803570 | 11/1987 |
| WO | WO 9621656 | 7/1996 |
| WO | WO 9716434 | 5/1997 |
| WO | WO 9858073 | 12/1998 |
| WO | WO 9965486 | 12/1999 |

OTHER PUBLICATIONS

Organic Letters, vol. 2, No. 25, pp. 4025-4027; (2000).
Lee, et al., "Enzymatic Resolution of Racemic Ibuprofen Esters: Effects of Organic Cosolvents and Temperature", *Journal of Fermentation and Bioengineering* 80(6), pp. 613-615 (1995), XP009022668.
Xie, et al., "Candida rugosa lipase catalyzed esterification of racemic ibuprofen with butanol; racemization of R-ibuprofen and chemical hydrolysis of S-ester formed", *Biotechnology Letters* 20(5), pp. 455-458 (1998), XP009022661.

*Primary Examiner*—Christopher R Tate
*Assistant Examiner*—Randall Winston
(74) *Attorney, Agent, or Firm*—Gregg C. Benson; John A. Wichtowski

(57) ABSTRACT

The present invention relates to a process for preparing 5-substitued-6-cyclic-5,6,7,8-tetrahydronaphthalen-2-ol compounds useful as an estrogen agonist.

9 Claims, No Drawings

ENZYMATIC RESOLUTION OF SELECTIVE ESTROGEN RECEPTOR MODULATORS

CROSS-REFERENCE TO RELATED APPLICATION

This is a division of U.S. patent application Ser. No. 09/850,545, filed on May 7, 2001 now U.S. Pat. No. 6,828,134, now allowed, which claims the benefit of U.S. provisional application No. 60/202,418, filed on May 8, 2000.

BACKGROUND OF THE INVENTION

The present invention relates to a process for preparing 5-substitued-6-cyclic-5,6,7,8-tetrahydronaphthalen-2-ol compounds useful as an estrogen agonist.

The value of naturally occurring estrogens and synthetic compounds demonstrating "estrogenic" activity has been in their medical and therapeutic uses. A traditional listing of the therapeutic applications for estrogens alone or in combination with other active agents includes: oral contraception; relief for the symptoms of menopause; prevention of threatened or habitual abortion; relief of dysmenorrhea; relief of dysfunctional uterine bleeding; an aid in ovarian development; treatment of acne; diminution of excessive growth of body hair in women (hirsutism); the prevention of cardiovascular disease; treatment of osteoporosis; treatment of prostatic carcinoma; and suppression of post-partum lactation [Goodman and Gilman, The Pharmacological Basis of Therapeutics (Seventh Edition) Macmillan Publishing Company, 1985, pages 1421-1423]. Accordingly, there has been increasing interest in finding newly synthesized compounds and new uses for previously known compounds which are demonstrably estrogenic, this is, able to mimic the action of estrogen in estrogen responsive tissue.

From the viewpoint of pharmacologists interested in developing new drugs useful for the treatment of human diseases and specific pathological conditions, it is most important to procure compounds with some demonstrable estrogen-like function but which are devoid of proliferative side-effects. Exemplifying this latter view, osteoporosis, a disease in which bone becomes increasingly more fragile, is greatly ameliorated by the use of fully active estrogens; however, due to the recognized increased risk of uterine cancer in patients chronically treated with active estrogens, it is not clinically advisable to treat osteoporosis in intact women with fully active estrogens for prolonged periods. Accordingly, estrogen agonists are the primary interest and focus.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. These cost the nation over $10 billion. Hip fractures are the most serious, with 5%-20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050.

Women are at greater risk of osteoporosis than men. Women experience a sharp acceleration of bone loss during the five years following menopause. Other factors that increase risk include smoking, alcohol abuse, a sedentary lifestyle and low calcium intake.

Estrogen is the agent of choice in preventing osteoporosis or post menopausal bone loss in women; it is the only treatment which unequivocally reduces fractures. However, estrogen stimulates the uterus and is associated with an increased risk of endometrial cancer. Although the risk of endometrial cancer is thought to be reduced by a concurrent use of a progestogen, there is still concern about possible increased risk of breast cancer with the use of estrogen.

SUMMARY OF THE INVENTION

The present invention relates to a process (Process A) for preparing a compound of the formula

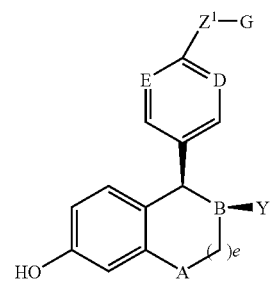

I wherein:
A is selected from $CH_2$ and NR;
B, D and E are independently selected from CH and N;
Y is
  (a) phenyl, optionally substituted With 1-3 substituents independently selected from $R^4$;
  (b) naphthyl, optionally substituted with 1-3 substituents independently selected from $R^4$;
  (c) $C_3$-$C_8$ cycloalkyl, optionally substituted with 1-2 substituents independently selected from $R^4$;
  (d) $C_3$-$C_8$ cycloalkynyl, optionally substituted with 1-2 substituents independently selected from $R^4$;
  (e) a five membered heterocycle containing up to two heteroatoms selected from the group consisting of —O—, —$NR^2$— and —$S(O)_n$—, optionally substituted with 1-3 substituents independently selected from $R^4$;
  (f) a six membered heterocycle containing up to two heteroatoms selected from the group consisting of —O—, —$NR^2$— and —$S(O)_n$— optionally substituted with 1-3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$—, $NR^2$— and —$S(O)_n$—, optionally substituted with 1-3 substituents independently selected from $R^4$;

$Z^1$ is
  (a) —$(CH_2)_p W(CH_2)_q$—;
  (b) —$O(CH_2)_p CR^5 R^6$—;
  (c) —$O(CH_2)_p W(CH_2)_q$;

(d) —OCHR²CHR³—; or
(e) —SCHR²CHR³—;
G is
(a) —NR⁷R⁸;
(b)

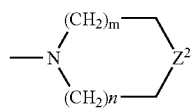

wherein n is 0, 1 or 2; m is 1, 2 or 3; $Z^2$ is —NH—, —O—, —S—, or —CH₂—; optionally fused on adjacent carbon atoms with one or two phenyl rings and, optionally independently substituted on carbon with one to three substituents and, optionally, independently on nitrogen with a chemically suitable substituent selected from $R^4$; or (c) a bicyclic amine containing five to twelve carbon atoms, either bridged or fused and optionally substituted with 1-3 substituents independently selected from $R^4$;

$Z^1$ and G in combination may be

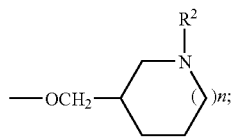

W is
(a) —CH₂—;
(b) —CH=CH—;
(c) —O—;
(d) —NR²—;
(e) —S(O)ₙ—;
(f)

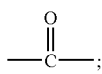

(g) —CR²(OH)—;
(h) —CONR²—;
(i) —NR²CO—;
(j)

or
(k) —C≡C—;
R is hydrogen or $C_1$-$C_6$ alkyl;
$R^2$ and $R^3$ are independently
(a) hydrogen; or
(b) $C_1$-$C_4$ alkyl;
$R^4$ is
(a) hydrogen;
(b) halogen;
(c) $C_1$-$C_6$ alkyl;
(d) $C_1$-$C_4$ alkoxy;
(e) $C_1$-$C_4$ acyloxy;
(f) $C_1$-$C_4$ alkylthio;
(g) $C_1$-$C_4$ alkylsulfinyl;
(h) $C_1$-$C_4$ alkylsulfonyl;
(i) hydroxy($C_1$-$C_4$)alkyl;
(j) aryl($C_1$-$C_4$)alkyl;
(k) —CO₂H;
(l) —CN;
(m) —CONHOR;
(n) —SO₂NHR;
(o) —NH₂;
(p) $C_1$-$C_4$ alkylamino;
(q) $C_1$-$C_4$ dialkylamino;
(r) —NHSO₂R;
(s) —NO₂;
(t) -aryl; or
(u) —OH.
$R^5$ and $R^6$ are independently $C_1$-$C_8$ alkyl or together form a $C_3$-$C_{10}$ carbocyclic ring;
$R^7$ and $R^8$ are independently
(a) phenyl;
(b) a $C_3$-$C_{10}$ carbocyclic ring, saturated or unsaturated;
(c) a $C_3$-$C_{10}$ heterocyclic ring containing up to two heteroatoms, selected from —O—, —N— and —S—;
(d) H;
(e) $C_1$-$C_6$ alkyl; or
(f) form a 3 to 8 membered nitrogen containing ring with $R^5$ or $R^6$;
$R^7$ and $R^8$ in either linear or ring form may optionally be substituted with up to three substituents independently selected from $C_1$-$C_6$ alkyl, halogen, alkoxy, hydroxy and carboxy;
a ring formed by $R^7$ and $R^8$ may be optionally fused to a phenyl ring;
e is 0, 1 or 2;
m is 1, 2 or 3;
n is 0, 1 or 2;
p is 0, 1, 2 or 3;
q is 0, 1, 2 or 3;
and optical and geometric isomers thereof;
comprising selectively deacetylating a compound of the formula

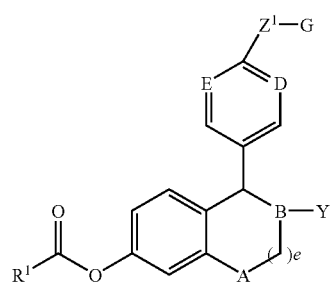

II wherein $R^1$ is ($C_1$-$C_6$)alkyl, ($C_2$-$C_6$)alkenyl, ($C_2$-$C_6$) alkynyl wherein the alkyl, alkenyl or alkynyl groups are optionally substituted by one to three halo, in the presence of a hydrolytic enzyme and an aqueous buffer solution.

The terms "GC-4, PS30, AY30, PGE, AK, N, L-10, AP-12, FAP-15, R-10, G, MAP10 and SAM II" are names of lipase enzymes used in this invention and sold by Amano Chemical Co., 1157 North Main Street, Lombard, Ill. 60148.

The terms "lipase from *Pseudomonas fluorescens*, lipase from *Candida cylindracea*, lipase from *Mucor miehei*, lipase from Wheat germ, lipase from *Rhizopus arrhizus*, lipase from *Mucor javanicus*, lipase from *Pseudomonas cepacia*, lipase from *Cadia lipolytica* and lipase from *Penicillium roqueforti*" are names of lipase enzymes used in this invention and sold by Fluka Chemical Co., 1001 West St. Paul Avenue, Milwaukee, Wis. 53233.

The terms "lipoprotein lipase ca#70-6571-01, and lipoprotein lipase ca# 70-1481-01" are names of lipase enzymes used in this invention and sold by Genzyme Chemical Co., One Kendall Square, Cambridge, Mass. 02139.

The terms "lipase from *Candida cylindracea*, lipase from *Chromobacterium viscosum*, lipase from *Mucor miehei*, lipase from Pancreatic, lipase from *Pseudomonas fluorescens* and lipase from *Rhizopus niveus*" are names of lipase enzymes used in this invention and sold by Recombinant Biocatalysis Chemical Co., 512 Elmwood Avenue, Sharon Hill, Pa. 19079.

The term "PPL, type II" is a name of a lipase enzyme used in this invention and sold by Sigma Chemical Co., P. O. Box 14508, St: Louis, Mo. 63178.

The term "Lip-300" is a name of a lipase enzyme used in this invention and sold by TOYOBO Chemical Co., 1450 Broadway, New York, N.Y. 10018.

The terms "immobilized, hog liver, esterase from Hog pancreas, esterase from *Thermoanaerobium brockii*, esterase from *Bacillus* sp and esterase from *Mucor miehI*" are names of esterase enzymes used in this invention and sold by Fluka Chemical Co., 1001 West St. Paul Avenue, Milwaukee, Wis. 53233.

The terms "cholesterol esterase from Porcine pancreas, cholesterol esterase from Bovine pancreas, cholesterol esterase from *Pseudonomas fluorescens*, cholesterol esterase from Porcine liver, cholesterol esterase from Rabbit liver, cholinesterase, cholinesterase from Electric eel, cholinesterase, choloylglycine hydrolase and Porcine liver E-3128" are names of esterase enzymes used in this invention and sold by Sigma Chemical Co., P. O. Box 14508, St. Louis, Mo. 63178.

The terms "cholesterin-esterase and cholesterin esterase from *Pseudonomas fluorescens*" are names of esterase enzymes used in this invention and sold by Boehringer Mannheim Chemical Co., 9115 Hague Road, Indianapolis, Ind. 46250.

The terms "cat I-1256, dog I 7379, eel I -1266, horse I9627, calf I7876, guinea pig I1631, mouse I8254, goat I2635, chicken I8001, sheep I0132, pigeon I8376, seal I7627, rattlesnake I9885, trout I5131, turtle I-0757, rat I1380, lungfish I7377, salmon I7502, eel (*electrophorus electricus*) I8380 and lemon shark I1130" are names of liver acetone powder enzymes used in this invention and sold by Sigma Chemical Co., P. O. Box 14508, St. Louis, Mo. 63178.

The present invention further relates to Process A wherein the hydrolytic enzyme is lipase.

The present invention further relates to Process A wherein the hydrolytic enzyme is esterase.

The present invention further relates to Process A wherein the hydrolytic enzyme is liver acetone powder.

The present invention further relates to Process A wherein the lipase is GC-4, PS30, AY30, PGE, AK, N, L-10, AP-12, FAP-15, R-10, G, MAP10, SAM II, lipase from *Pseudomonas fluorescens*, lipase from *Candida cylindracea*, Lip-300, lipase from *Chromobacterium viscosum*, lipase from *Mucor miehei*, lipase from Pancreatic, *Pseudomonas fluorescens*, lipase from *Rhizopus niveus*, PPL, type II, lipase from Wheat germ, lipase from *Rhizopus arrhizus*, lipase from *Mucor javanicus*, lipase from *Pseudomonas cepacia*, lipase from *Cadia lipolytica*, lipase from *Penicillium roqueforti*, lipoprotein lipase ca#70,6571-01, lipase from Porcine pancreas and lipoprotein lipase ca# 70-1481-01.

The present invention further relates to Process A wherein the esterase, is PLE-A, immobilized, hog liver, esterase from Hog pancreas, Porcine liver E-3128, cholesterin-esterase, cholesterol esterase from *Pseudonomas fluorescens*, cholesterol esterase from Porcine pancreas, cholesterol esterase from Bovine pancreas, cholesterol esterase from *Pseudonomas fluorescens*, cholesterol esterase from Porcine liver, cholesterol esterase from Rabbit liver, cholinesterase, cholinesterase from Electric eel, cholinesterase, choloylglycine hydrolase, esterase from *Themoanaerobium brockii*, esterase from *Bacillus* sp and esterase from *Mucor miehi*.

The present invention further relates to Process A wherein the liver acetone powder is cat I-1256, dog I7379, eel I-1266, horse I9627, calf I7876, guinea pig I1631, mouse I8254, goat I2635, chicken I8001, sheep I0132, pigeon I8376, seal I7627, rattlesnake I9885, trout I5131, turtle I-0757, rat I1380, lungfish I7377, salmon I7502, eel (*electrophorus electricus*) I8380 and lemon shark I1130.

The present invention further relates to Process A wherein the hydrolytic enzyme is immobilized on a solid support.

The present invention further relates to Process A wherein the hydrolytic enzyme is in pure crystalline form.

The present invention further relates to Process A wherein the aqueous buffer solution is a phosphate, citric acid or boronic acid solution.

The present invention further relates to Process A wherein the aqueous buffer solution has a pH between a pH of about 6 to a pH of about 8.

The present invention relates to a process for preparing a compound of the formula

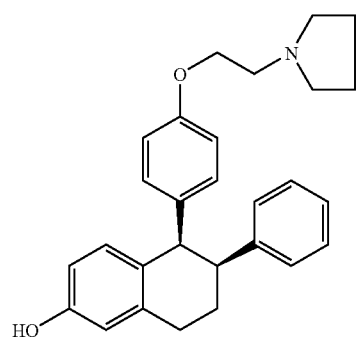

VII comprising selectively deacetylating a compound of the formula

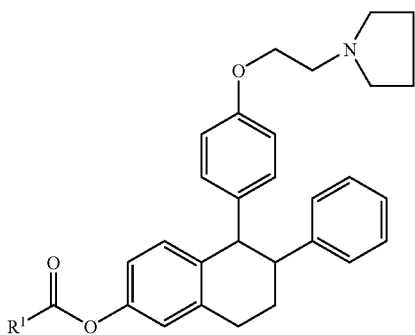

VIII wherein $R^1$ is $(C_1-C_6)$alkyl, $(C_2-C_6)$alkenyl, $(C_2-C_6)$alkynyl wherein the alkyl, alkenyl or alkynyl groups are optionally substituted by one to three halo in the presence of a hydrolytic enzyme and an aqueous buffer solution.

The present invention relates to a process (Process B) for preparing a compound of the formula:

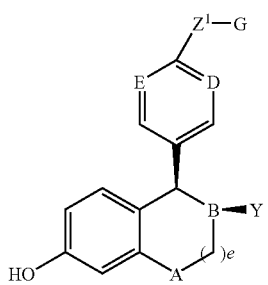

I wherein:
A is selected from $CH_2$ and NR;
B, D and E are independently selected from CH and N;
Y is
  (a) phenyl, optionally substituted with 1-3 substituents independently selected from $R^4$;
  (b) naphthyl, optionally substituted with 1-3 substituents independently selected from $R^4$;
  (c) $C_3-C_8$ cycloalkyl, optionally substituted with 1-2 substituents independently selected from $R^4$;
  (d) $C_3-C_8$ cycloalkynyl, optionally substituted with 1-2 substituents independently selected from $R^4$;
  (e) a five membered heterocycle containing up to two heteroatoms selected from the group consisting of —O—, —$NR^2$— and —$S(O)_n$—, optionally substituted with 1-3 substituents independently selected from $R^4$;
  (f) a six membered heterocycle containing up to two heteroatoms selected from the group consisting of —O—, —$NR^2$— and —$S(O)_n$— optionally substituted with 1-3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$—, $NR^2$— and —$S(O)_n$—, optionally substituted with 1-3-substituents independently selected from $R^4$;

$Z^1$ is
  (a) —$(CH_2)_p W(CH_2)_q$—;
  (b) —$O(CH_2)_p CR^5 R^6$—;
  (c) —$O(CH_2)_p W(CH_2)_q$;
  (d) —$OCHR^2 CHR^3$; or
  (e) —$SCHR^2 CHR^3$—;

G is
  (a) —$NR^7 R^8$;
  (b)

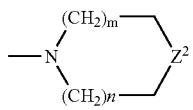

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
  (c) a bicyclic amine containing five to twelve carbon atoms, either bridged or fused and optionally substituted with 1-3 substituents independently selected from $R^4$;

$Z^1$ and G in combination may be

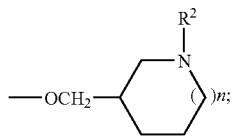

W is
  (a) —$CH_2$—;
  (b) —CH=CH—;
  (c) —O—;
  (d) —$NR^2$;
  (e) —$S(O)_n$—;
  (f)

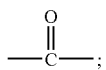

(g) —$CR^2(OH)$—;
  (h) —$CONR^2$;
  (i) —$NR^2 CO$;
  (j)

or
  (k) —C≡C—;

R is hydrogen or $C_1$-$C_6$ alkyl;
$R^2$ and $R^3$ are independently
  (a) hydrogen; or
  (b) $C_1$-$C_4$ alkyl;
$R^4$ is
  (a) hydrogen;
  (b) halogen;
  (c) $C_1$-$C_6$ alkyl;
  (d) $C_1$-$C_4$ alkoxy;
  (e) $C_1$-$C_4$ acyloxy;
  (f) $C_1$-$C_4$ alkylthio;
  (g) $C_1$-$C_4$ alkylsulfinyl;
  (h) $C_1$-$C_4$ alkylsulfonyl;
  (i) hydroxy($C_1$-$C_4$)alkyl;
  (j) aryl($C_1$-$C_4$)alkyl;
  (k) —$CO_2H$;
  (l) —CN;
  (m) —CONHOR;
  (n) —$SO_2NHR$;
  (o) —$NH_2$;
  (p) $C_1$-$C_4$ alkylamino;
  (q) $C_1$-$C_4$ dialkylamino;
  (r) —$NHSO_2R$;
  (s) —$NO_2$;
  (t) -aryl; or
  (u) —OH.
$R^5$ and $R^6$ are independently $C_1$-$C_8$ alkyl or together form a $C_1$-$C_{10}$ carbocyclic ring;
$R^7$ and $R^8$ are independently
  (a) phenyl;
  (b) a $C_3$-$C_{10}$ carbocyclic ring, saturated or unsaturated;
  (c) a $C_3$-$C_{10}$ heterocyclic ring containing up to two heteroatoms, selected from —O—, —N— and —S—;
  (d) H;
  (e) $C_1$-$C_6$ alkyl; or
  (f) form a 3 to 8 membered nitrogen containing ring with $R^5$ or $R^6$;
$R^7$ and $R^8$ in either linear or ring form may optionally be substituted with up to three substituents independently selected from $C_1$-$C_6$ alkyl, halogen, alkoxy, hydroxy and carboxy;
a ring formed by $R^7$ and $R^8$ may be optionally fused to a phenyl ring;
e is 0, 1 or 2;
m is 1, 2 or 3;
n is 0, 1 or 2;
p is 0, 1, 2 or 3;
q is 0, 1, 2 or 3;
and optical and geometric isomers thereof;
comprising enzymatically resolving of a compound of the formula

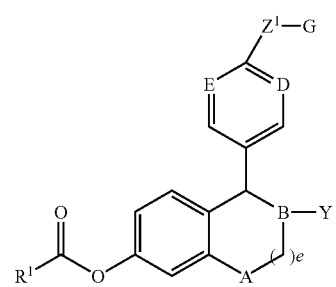

II wherein $R^1$ is ($C_1$-$C_6$)alkyl, ($C_2$-$C_6$)alkenyl, ($C_2$-$C_6$)alkynyl wherein the alkyl, alkenyl or alkynyl groups are optionally substituted by one to three halo in the presence of a lipase and an aqueous buffer solution; and
(b) reacting the compound of formula IV so formed

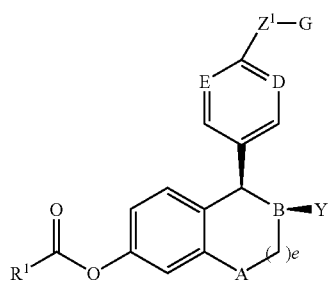

IV wherein $R^1$ is as defined above, with a base in the presence of a polar protic solvent.

The present invention further relates to Process B wherein the aqueous buffer solution is a phosphate, citric acid or boronic acid solution.

The present invention further relates to Process B wherein the lipase from *Mucor miehei*.

The present invention further relates to Process B wherein the base is sodium methoxy, sodium hydroxide, lithium hydroxide or potassium hydroxide.

The present invention further relates to Process B wherein the polar protic solvent is methanol, ethanol or water.

The present invention further relates to Process B wherein the lipase is immobilized on a solid support.

The present invention further relates to Process B wherein the lipase is a cross-linked enzyme.

The present invention further relates to Process B wherein the lipase is in pure crystalline form.

The present invention relates to a process for preparing a compound of the formula

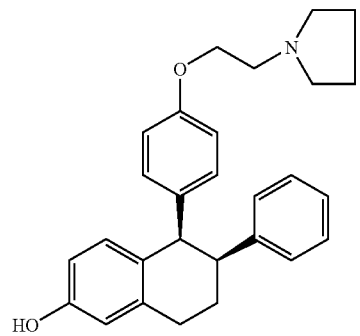

VII comprising enzymatically resolving of a compound of the formula

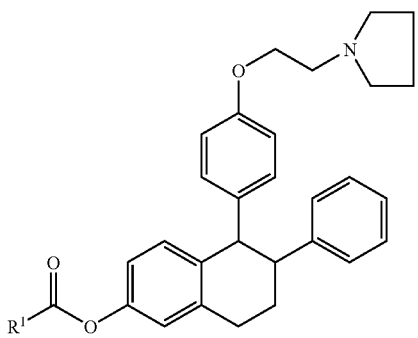

VIII wherein $R^1$ is $(C_1-C_6)$alkyl, $(C_2-C_6)$alkenyl, $(C_2-C_6)$alkynyl wherein the alkyl, alkenyl or alkynyl groups are optionally substituted by one to three halo in the presence of a lipase and an aqueous buffer solution; and (b) reacting the compound of Formula X so formed

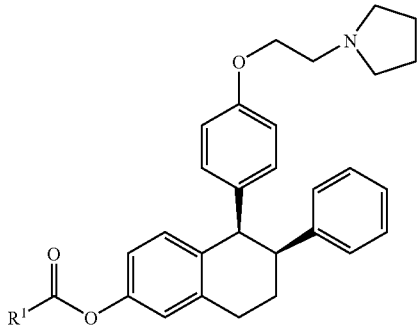

X wherein $R^1$ is as defined above, with a base in the presence of a polar protic solvent.

The present invention relates to a process (Process C) for preparing a compound of the formula:

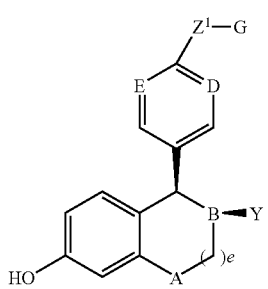

I wherein:
A is selected from $CH_2$ and NR;
B, D and E are independently selected from CH and N;
Y is
(a) phenyl, optionally substituted with 1-3 substituents independently selected from $R^4$;

(b) naphthyl, optionally substituted with 1-3 substituents independently selected from $R^4$;
(c) $C_3-C_8$ cycloalkyl, optionally substituted with 1-2 substituents independently selected from $R^4$;
(d) $C_3-C_8$ cycloalkynyl, optionally substituted with 1-2 substituents independently selected from $R^4$;
(e) a five membered heterocycle containing up to two heteroatoms selected from the group consisting of —O—, —$NR^2$— and —$S(O)_n$—, optionally substituted with 1-3 substituents independently selected from $R^4$;
(f) a six membered heterocycle containing up to two heteroatoms selected from the group consisting of —O—, —$NR^2$— and —$S(O)_n$— optionally substituted with 1-3 substituents independently selected from $R^4$; or
(g) a bicyclic ring system consisting of a five or six membered heterocyclic ring fused to a phenyl ring, said heterocyclic ring containing up to two heteroatoms selected from the group consisting of —O—, —$NR^2$—, $NR^2$— and —$S(O)_n$—, optionally substituted with 1-3 substituents independently selected from $R^4$;

$Z^1$ is
(a) —$(CH_2)_pW(CH_2)_q$—;
(b) —$O(CH_2)_pCR^5R^6$—;
(c) —$O(CH_2)_pW(CH_2)_q$;
(d) —$OCHR^2CHR^3$—; or
(e) —$SCHR^2CHR^3$—;

G is
(a) —$NR^7R^8$;
(b)

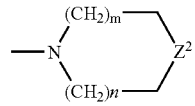

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
(c) a bicyclic amine containing five to twelve carbon atoms, either bridged or fused and optionally substituted with 1-3 substituents independently selected from $R^4$;

$Z^1$ and G in combination may be

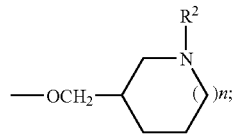

W is
(a) —$CH_2$—;
(b) —CH═CH—;
(c) —O—;
(d) —$NR^2$—;
(e) —$S(O)_n$—;

(f)

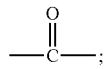

(g) —CR²(OH)—;
(h) —CONR²;
(i) —NR²CO;
(j)

or
(k) —C≡C—;
R is hydrogen or C—C₆ alkyl;
R² and R³ are independently
  (a) hydrogen; or
  (b) $C_1$-$C_4$ alkyl;
R⁴ is
  (a) hydrogen;
  (b) halogen;
  (c) $C_1$-$C_6$ alkyl;
  (d) $C_1$-$C_4$ alkoxy;
  (e) $C_1$-$C_4$ acyloxy;
  (f) $C_1$-$C_4$ alkylthio;
  (g) $C_1$-$C_4$ alkylsulfinyl;
  (h) $C_1$-$C_4$ alkylsulfonyl;
  (i) hydroxy($C_1$-$C_4$)alkyl;
  (l) aryl($C_1$-$C_4$)alkyl;
  (k) —CO₂H;
  (l) —CN;
  (m) —CONHOR;
  (n) —SO₂NHR;
  (o) —NH₂;
  (p) $C_1$-$C_4$ alkylamino;
  (q) $C_1$-$C_4$ dialkylamino;
  (r) —NHSO₂R;
  (s) —NO₂;
  (t) -aryl; or
  (u) —OH.
R⁵ and R⁶ are independently $C_1$-$C_8$ alkyl or together form a $C_3$-$C_{10}$ carbocyclic ring;
R⁷ and R⁸ are independently
  (a) phenyl;
  (b) a $C_3$-$C_{10}$ carbocyclic ring, saturated or unsaturated;
  (c) a $C_3$-$C_{10}$ heterocyclic ring containing up to two heteroatoms, selected from —O—, —N— and —S—;
  (d) H;
  (e) $C_1$-$C_6$ alkyl; or
  (f) form a 3 to 8 membered nitrogen containing ring with R⁵ or R⁶;
R⁷ and R⁸ in either linear or ring form may optionally be substituted with up to three substituents independently selected from $C_1$-$C_6$ alkyl, halogen, alkoxy, hydroxy and carboxy;
a ring formed by R⁷ and R⁸ may be optionally fused to a phenyl ring;
e is 0, 1 or 2;
m is 1, 2 or 3;
n is 0, 1 or 2;
p is 0, 1, 2 or 3;
q is 0, 1, 2 or 3;
and optical and geometric isomers thereof;
comprising enzymatically resolving of a compound of the formula

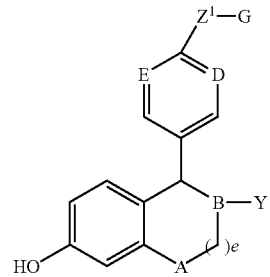

VI in the presence of a lipase and an acetylating agent, and
(b) reacting the compound of formula IV so formed

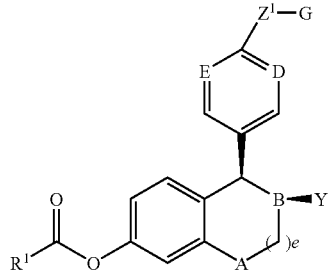

IV wherein R¹ is $(C_1$-$C_6)$alkyl, $(C_2$-$C_6)$alkenyl, $(C_2$-$C_6)$alkynyl wherein the alkyl, alkenyl or alkynyl groups are optionally substituted by one to three halo, with a base in the presence of a polar protic solvent.

The present invention further relates to Process C wherein the hydrolytic enzyme is a lipase.

The present invention further relates to Process C wherein the lipase is GC-4, PS30, AY30, PGE, AK, N, L-10, AP-12, FAP-15, R-10, G, MAP10, SAM II, lipase from *Pseudomonas fluorescens*, lipase from *Candida cylindracea*, Lip-300, lipase from *Chromobacterium viscosum*, lipase from *Mucor miehei*, lipase from Pancreatic, lipase from *Pseudomonas fluorescens*, lipase from *Rhizopus niveus*, PPL, type II, lipase from Wheat germ, lipase from *Rhizopus arrhizus*, lipase from *Mucor javanicus*, lipase from *Pseudomonas cepacia*, lipase from *Cadia lipolytica*, lipase from *Penicillium roqueforti*, lipoprotein lipase ca#70-6571-01, lipase from Porcine pancreas, and lipoprotein lipase ca# 70-1481-01.

The present invention further relates to Process C wherein the acetylating agent is ethyl acetate, vinyl acetate, chloroacetate or trifluoroacetate.

The present invention further relates to Process C wherein the base is sodium methoxy, sodium hydroxide, lithium hydroxide or potassium hydroxide.

The present invention further relates to Process C wherein the polar protic solvent is methanol, ethanol or water.

The present invention further relates to Process C wherein the lipase is immobilized on a solid support.

The present invention further relates to Process C wherein the lipase is a cross-linked enzyme.

The present invention further relates to Process C wherein the lipase is in pure crystalline form.

The present invention relates to a process for preparing a compound of the formula

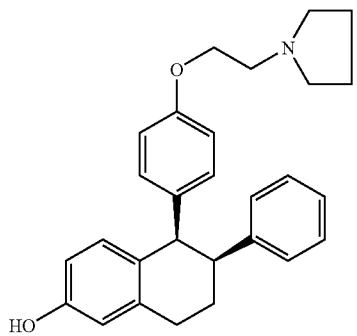

VII comprising enzymatically resolving of a compound of the formula

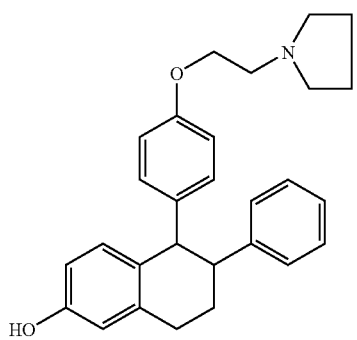

XII in the presence of a lipase and acetylating agent, and (b) reacting the compound of Formula X so formed

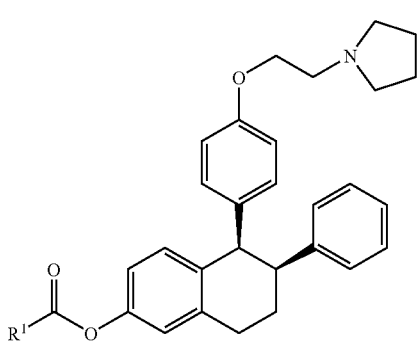

X wherein $R^1$ is $(C_1$-$C_6)$alkyl, $(C_2$-$C_6)$alkenyl, $(C_2$-$C_6)$alkynyl wherein the alkyl, alkenyl or alkynyl groups are optionally substituted by one to three halo, with a base in the presence of a polar protic solvent.

The present invention relates to a process (Process D) for preparing a compound of the formula:

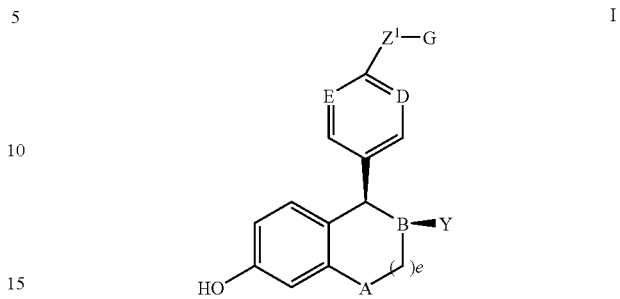

I wherein:
A is selected from $CH_2$ and NR;
B, D and E are independently selected from CH and N;
Y is
   (a) phenyl, optionally substituted with 1-3 substituents independently selected from $R^4$;
   (b) naphthyl, optionally substituted with 1-3 substituents independently selected from $R^4$;
   (c) $C_3$-$C_8$ cycloalkyl, optionally substituted with 1-2 substituents independently selected from $R^4$;
   (d) $C_3$-$C_8$ cycloalkynyl, optionally substituted with 1-2 substituents independently selected from $R^4$;
   (e) a five membered heterocycle containing up to two heteroatoms selected from the group consisting of —O—, —$NR^2$— and —$S(O)_n$—, optionally substituted with 1-3 substituents independently selected from $R^4$;
   (f) a six membered heterocycle containing up to two heteroatoms selected from the group consisting of —O—, —$NR^2$— and —$S(O)_n$— optionally substituted with 1-3 substituents independently selected from $R^4$; or
   (g) a bicyclic ring system consisting of a five or six membered heterocyclic ring fused to a phenyl ring, said heterocyclic ring containing up to two heteroatoms selected from the group consisting of —O—, —$NR^2$—, $NR^2$— and —$S(O)_n$—, optionally substituted with 1-3 substituents independently selected from $R^4$;
$Z^1$ is
   (a) —$(CH_2)_p W(CH_2)_q$—;
   (b) —$O(CH_2)_p CR^5 R^6$—;
   (c) —$O(CH_2)_p W(CH_2)_q$—;
   (d) —$OCHR^2 CHR^3$—; or
   (e) —$SCHR^2 CHR^3$—;
G is
   (a) —$NR^7 R^8$;
   (b)

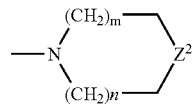

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from R⁴; or
(c) a bicyclic amine containing five to twelve carbon atoms, either bridged or fused and optionally substituted with 1-3 substituents independently selected from R⁴;

Z¹ and G in combination may be

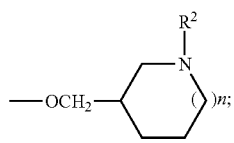

W is
(a) —CH₂—;
(b) —CH=CH—;
(c) —O—;
(d) —NR²—;
(e) —S(O)ₙ—;
(f)

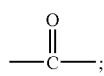

(g) —CR²(OH)—;
(h) —CONR²—;
(i) —NR²CO—;
(j)

or
(k) —C≡C—;

R is hydrogen or $C_1$-$C_6$ alkyl;
R² and R³ are independently
(a) hydrogen; or
(b) $C_1$-$C_4$ alkyl;

R⁴ is
(a) hydrogen;
(b) halogen;
(c) $C_1$-$C_6$ alkyl;
(d) $C_1$-$C_4$ alkoxy;
(e) $C_1$-$C_4$ acyloxy;
(f) $C_1$-$C_4$ alkylthio;
(g) $C_1$-$C_4$ alkylsulfinyl;
(h) $C_1$-$C_4$ alkylsulfonyl;
(i) hydroxy($C_1$-$C_4$)alkyl;
(j) aryl($C_1$-$C_4$)alkyl;
(k) —CO₂H;
(l) —CN;
(m) —CONHOR;
(n) —SO₂NHR;
(o) —NH₂;
(p) $C_1$-$C_4$ alkylamino;
(q) $C_1$-$C_4$ dialkylamino;
(r) —NHSO₂R;
(s) —NO₂;
(t) -aryl; or
(u) —OH.

R⁵ and R⁶ are independently $C_1$-$C_8$ alkyl or together form a $C_3$-$C_{10}$ carbocyclic ring;

R⁷ and R⁸ are independently
(a) phenyl;
(b) a $C_3$-$C_{10}$ carbocyclic ring, saturated or unsaturated;
(c) a $C_3$-$C_{10}$ heterocyclic ring containing up to two heteroatoms, selected from —O—, —N— and —S—;
(d) H;
(e) $C_1$-$C_6$ alkyl; or
(f) form a 3 to 8 membered nitrogen containing ring with R⁵ or R⁶;

R⁷ and R⁸ in either linear or ring form may optionally be substituted with up to three substituents independently selected from $C_1$-$C_6$ alkyl, halogen, alkoxy, hydroxy and carboxy;

a ring formed by R⁷ and R⁸ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof;
comprising enzymatically resolving of a compound of the formula

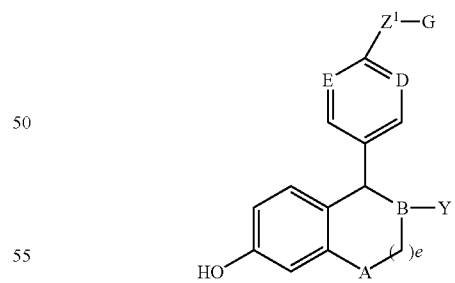

VI in the presence of lipase.

The present invention further relates to Process D wherein the lipase is *Mucor miehei*.

The present invention further relates to Process D wherein the lipase is immobilized on a solid support.

The present invention further relates to Process D wherein the lipase is a cross-linked enzyme.

The present invention further relates to Process D wherein the lipase is in pure crystalline form.

The present invention relates to a process for preparing a compound of the formula
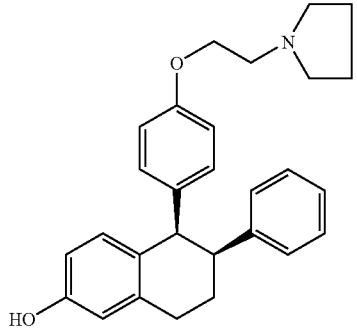
VII
comprising enzymatically resolving of a compound of the formula
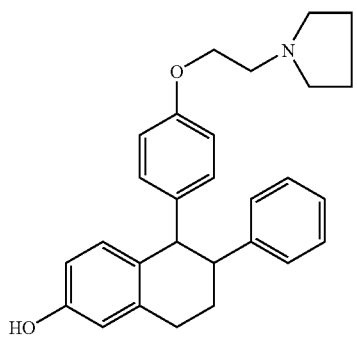
XII
in the presence of lipase.
DETAILED DESCRIPTION OF THE INVENTION
Scheme 1
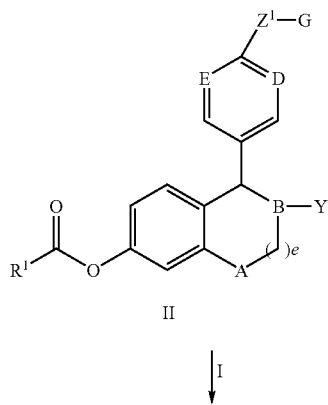
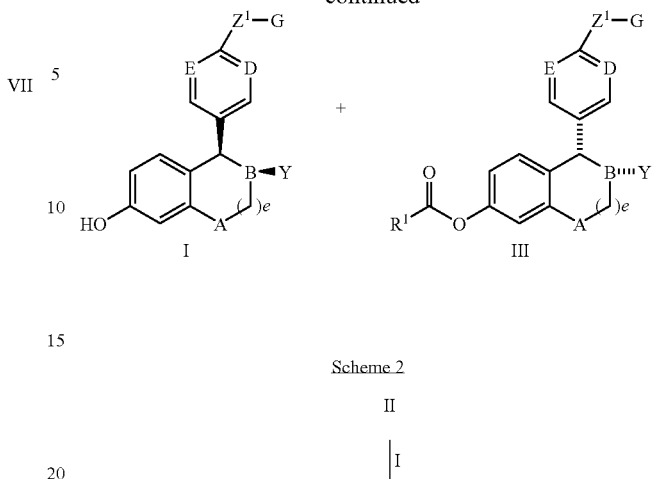
Scheme 2
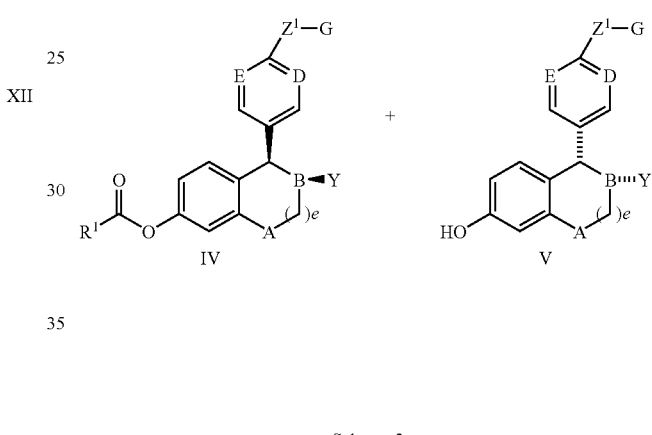
Scheme 3
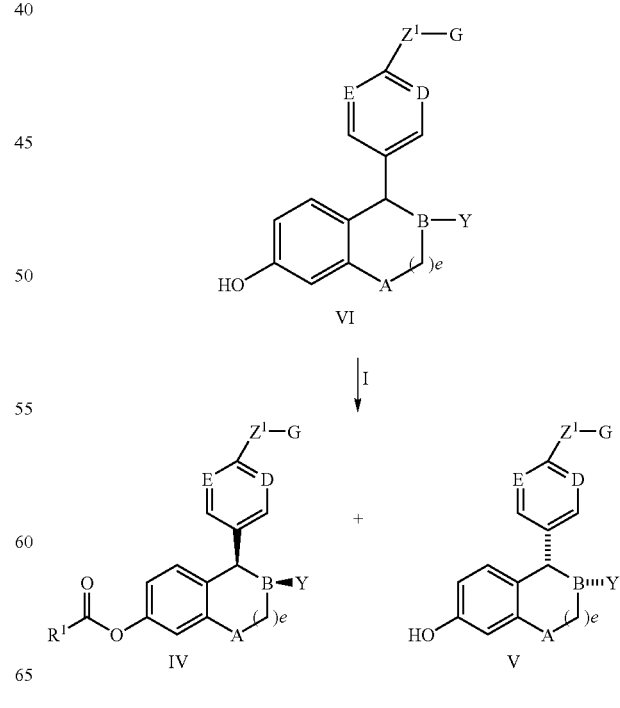

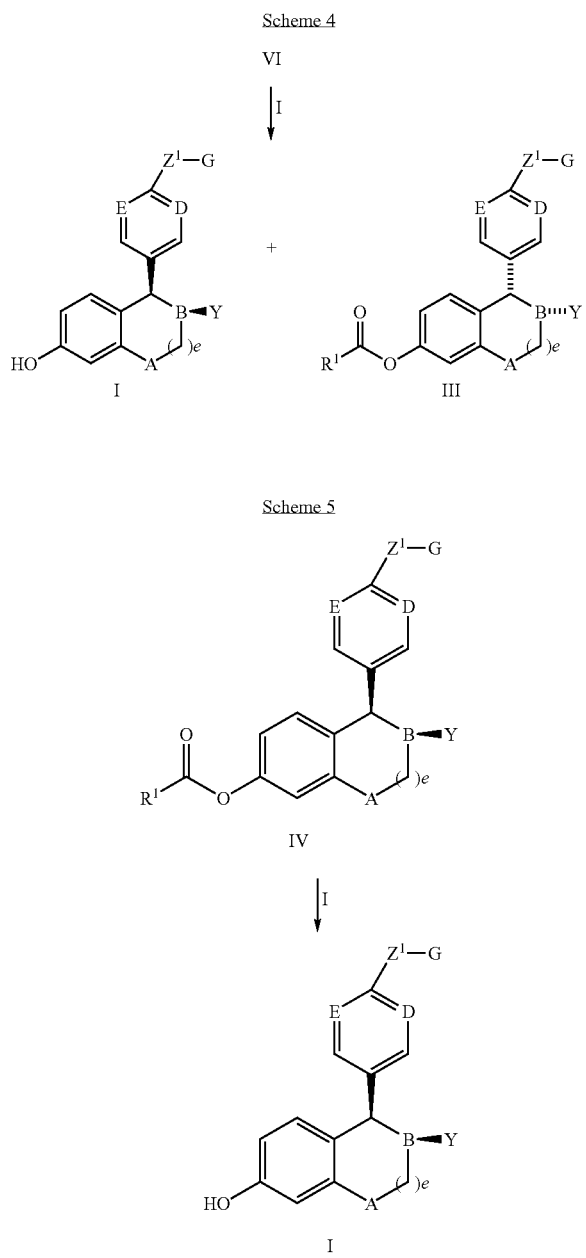

The starting materials for the present invention are prepared according to U.S. Pat. No. 5,552,412, which is incorporated by reference in its entirety.

In reaction 1 of Scheme 1 the compound of formula II is converted to the corresponding compounds of formulas I and, III by enzymatic resolution of II in the presence of a hydrolytic enzyme, mobilized or immobilized on different solid support, a cross-linked enzyme or a crystallized enzyme. Hydrolytic enzymes include (a) lipase (GC-4, PS30, AY30, PGE, AK, N, L-10, AP-12, FAP-15, R-10, G, MAP10, SAM II, lipase from *Pseudomonas fluorescens*, lipase from *Candida cylindracea*, Lip-300, lipase from *Chromobacterium viscosum*, lipase from *Mucor miehei*, lipase from Pancreatic, lipase from *Pseudomonas fluorescens*, lipase from *Rhizopus niveus*, PPL, type II, lipase from Wheat germ, lipase from *Rhizopus arrhizus*, lipase from *Mucor javanicus*, lipase from *Pseudomonas cepacia*, lipase from *Cadia lipolytica*, lipase from *Penicillium roqueforti*, lipoprotein lipase ca#70-6571-01, lipase from Porcine pancreas, and lipoprotein lipase ca# 70-1481-01), (b) esterase (PLE-A, immobilized, hog liver, esterase from Hog pancreas, Porcine liver E-3128, cholesterin-esterase, cholesterol esterase from *Pseudonomas fluorescens*, cholesterol esterase from Porcine pancreas, cholesterol esterase from Bovine pancreas, cholesterol esterase from *Pseudonomas fluorescens*, cholesterol esterase from Porcine liver, cholesterol esterase from Rabbit liver, cholinesterase, cholinesterase from Electric eel, cholinesterase, choloylglycine hydrolase, esterase from *Thermoanaerobium brockii*, esterase from *Bacillus* sp and esterase from *Mucor miehei*) or (c) liver acetone powder (cat I-1256, dog I7379, eel I-1266, horse I9627, calf I7876, guinea pig I1631, mouse I8254, goat I2635, chicken I8001, sheep I0132, pigeon I8376, seal I7627, rattlesnake I9885, trout I5131, turtle I-0757, rat I1380, lungfish I7377, salmon I7502, eel (*electrophorus electricus*) I8380 and lemon shark I1130). The reaction is carried out in an aqueous buffer solution, such as a phosphate, citric acid or boronic acid buffer, with or without an organic solvent, such as methylene chloride, tetrahyfrofuran, acetone, dimethyl formamide or dioxane. The buffer solution has a pH of about 6 to a pH of about 8, preferably a pH of about 7. The reaction is stirred at a temperature between room temperature to about 65° C., preferably about 25° C. to about 40° C., for a time period dependent upon the enzyme employed and the desired enantiomeric excess conversion of the racemic mixture.

In reaction I of Scheme 2, the compound of formula II is converted to the corresponding compounds of formulas IV and V by enzymatic resolution of II with a lipase, such as *Mucor miehei*, according to the procedure described above in reaction I of Scheme 1.

In reaction I of Scheme 3, the compound of formula VI is converted to the corresponding compounds of formulas IV and V by enzymatic resolution of VI with a lipase (GC-4, PS30, AY30, PGE, AK, N, L-10, AP-12, FAP-15, R-10, G, MAP10, SAM II, lipase from *Pseudomonas fluorescens*, lipase from cylindracea, Lip-300, lipase from *Candida cylindracea*, lipase from *Chromobacterium viscosum*, lipase from *Mucor miehei*, lipase from Pancreatic, lipase from *Pseudomonas fluorescens*, lipase from *Rhizopus niveus*, PPL, type II, lipase from Wheat germ, lipase from *Rhizopus arrhizus*, lipase from *Mucor javanicus*, lipase from *Pseudomonas cepacia*, lipase from *Cadia lipolytica*, lipase from *Penicillium roqueforti*, lipoprotein lipase ca#70-6571-01, lipase from Porcine pancreas, and lipoprotein lipase ca# 70-1481-01) in the presence of an acetylating agent, such as ethyl acetate, vinyl acetate, chloroacetate or trifluoroacetate. The reaction is stirred in an aprotic solvent, such as methylene chlorine, ethylene glycol, dimethyl ether, dichloroethane, hexane, tetrahydrofuran and dioxane, at a temperature between room temperature to about 65° C., preferabloy about 25° C. to about 40° C., for a time period dependent upon the enzyme employed and the desired enantiomeric excess conversion of the racemic mixture.

In reaction I of Scheme 4, the compound of formula VI is converted to the corresponding compounds of formulas of I and III by enzymatic resolution of II with a lipase, such as *Mucor miehei*. The reaction is stirred in an aprotic solvent, such as methylene chlorine, ethylene glycol, dimethyl ether, dichloroethane, hexane, tetrahydrofuran and dioxane, at a temperature between room temperature to about 65° C., preferably about 25° C. to about 40° C., for a time period dependant upon the enzyme employed and the desired enantiomeric excess conversion of the racemic mixture.

In reaction I of Scheme 5, the compound of formula IV is converted to the corresponding compound of formula I by deacetylating IV with a base, such as sodium methoxy, sodium hydroxide, lithium hydroxide or potassium hydroxide, in a polar protic solvent, such as methanol ethanol or water. The reaction is stirred at room temperature for a time period between about 1 hour and about 24 hours, preferably about 6 hours.

EXAMPLE 1

(−)Cis-6(S)-Phenyl-5(R)-[4-(2-pyrrolidin-1-yl-ethoxy)Phenyl]-5,6,7,8-tetrahydronaphthalen-2-ol A mixture of the racemic acetylate, corresponding to the title compound, cholesterol esterase from Porcine pancreas (C-9530), commercially sold by SIGMA, and a 0.1M phosphate buffer, having a pH of 7, was stirred at room temperature. The enzymatic resolution was stopped at 30 to 50% conversion and monitored by high pressure liquid chromatography. The solution was then extracted with ethyl acetate. The organic layer was washed with water followed by brine, dried over magnesium sulfate, filtered and concentrated to yield a brown solid. The residue was dissolved in methylene chloride and purified by flash chromatography over $SiO_2$ with methylene chloride/methanol in a 9:1 ratio and a few drops of $NH_4OH$ as the elutant to yield the product as an off-white foam. $^1H$ NMR (250M Hz, $CDCL_3$): d 7.04 (m, 3H), 6.74 (m, 2H), 6.63 (d, J=8.3 Hz, 2H), 6.50 (m, 3H), 6.28 (d, J=8.6 Hz, 2H), 4.14 (d, J=4.9 Hz, 1H), 3.94 (t, J=5.3 Hz, 2H), 3.249 dd, J=12.5, 4.1 Hz, 1H), 2.59 (m, 4H), 2.78 (m, 1H), 1.88 (m, 4H), 1.68 (m, 1H). The optical purity of the product was determined by chiral HPLC assay.

What is claimed is:

1. A process for preparing a compound of the formula:

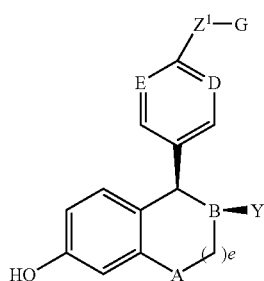

I wherein:
A is selected from $CH_2$ and NR;
B, D and F are independently selected from CH and N;
Y is
  (a) phenyl, optionally substituted with 1-3 substituents independently selected from $R^4$;
  (b) naphthyl, optionally substituted with 1-3 substituents independently selected from $R^4$;
  (c) $C_3$-$C_8$ cycloalkyl, optionally substituted with 1-2 substituents independently selected from $R^4$;
  (d) $C_3$-$C_8$ cycloalkynyl, optionally substituted with 1-2 substituents independently selected from $R^4$;
  (e) a five membered heterocycle containing up to two heteroatoms selected from the group consisting of —O—, —$NR^2$— and —$S(O)_n$—, optionally substituted with 1-3 substituents independently selected from $R^4$;
  (f) a six membered heterocycle containing up to two heteroatoms selected from the group consisting of —O—, —$NR^2$— and —$S(O)_n$— optionally substituted with 1-3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$—, $NR^2$— and —$S(O)_n$—, optionally substituted with 1-3 substituents independently selected from $R^4$;

$Z^1$ is
  (a) —$(CH_2)_p W (CH_2)_q$—;
  (b) —$O(CH_2)_p CR^5 R^6$—;
  (c) —$O(CH_2)_p W(CH_2)_q$;
  (d) —$OCHR^2 CHR^3$—; or
  (e) —$SCHR^2 CHR^3$—;

G is
  (a) —$NR^7 R^8$;
  (b)

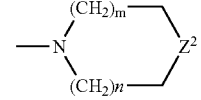

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
  (c) a bicyclic amine containing five to twelve carbon atoms, either bridged or fused and optionally substituted with 1-3 substituents independently selected from $R^4$;

$Z^1$ and G in combination may be

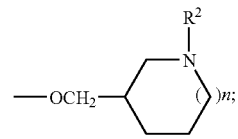

W is
  (a) —$CH_2$—;
  (b) —CH=CH—;
  (c) —O—;
  (d) —$NR^2$—;
  (e) —$S(O)_n$—;
  (f)

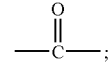

(g) —$CR^2(OH)$—;
  (h) —$CONR^2$—;

(i) —NR²CO—;
(j)

or
(k) —C≡C—;
R is hydrogen or $C_1$-$C_6$ alkyl;
$R^2$ and $R^3$ are independently
  (a) hydrogen; or
  (b) $C_1$-$C_4$ alkyl;
$R^4$ is
  (a) hydrogen;
  (b) halogen;
  (c) $C_1$-$C_6$ alkyl;
  (d) $C_1$-$C_4$alkoxy;
  (e) $C_1$-$C_4$ acyloxy;
  (f) $C_1$-$C_4$ alkylthio;
  (g) $C_1$-$C_4$ alkylsulfinyl;
  (h) $C_1$-$C_4$ alkylsulfonyl;
  (i) hydroxy ($C_1$-$C_4$)alkyl;
  (j) aryl ($C_1$-$C_4$)alkyl;
  (k) —$CO_2$H;
  (l) —CN;
  (m) —CONHOR;
  (n) —$SO_2$NHR;
  (o) —$NH_2$;
  (p) $C_1$-$C_4$ alkylamino;
  (q) $C_1$-$C_4$ dialkylamino;
  (r) —$NHSO_2$R;
  (s) —$NO_2$;
  (t) -aryl; or
  (u) —OH,
$R^5$ and $R^6$ are independently $C_1$-$C_8$ alkyl or together form a $C_3$-$C_{10}$ carbocyclic ring;
$R^7$ and $R^8$ are independently
  (a) phenyl;
  (b) a $C_3$-$C_{10}$ carbocyclic ring, saturated or unsaturated;
  (c) a $C_3$-$C_{10}$ heterocyclic ring containing up to two heteroatoms, selected from —O—, —N— and —S—;
  (d) H;
  (e) $C_1$-$C_6$ alkyl; or
  (f) form a 3 to 8 membered nitrogen containing ring with $R^5$ or $R^6$;
$R^7$ and $R^8$ in either linear or ring form may optionally be substituted with up to three substituents independently selected from $C_1$-$C_6$ alkyl, halogen, alkoxy, hydroxy and carboxy;
a ring formed by $R^7$ and $R^8$ may be optionally fused to a phenyl ring;
e is 0, 1 or 2;
m is 1, 2 or 3;
n is 0, 1 or 2;
p is 0, 1, 2 or 3;
q is 0, 1, 2 or 3;
and optical and geometric isomers thereof;

comprising enzymatically resolving of a compound of the formula

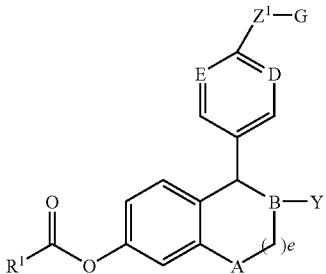

II wherein $R^1$ is ($C_1$-$C_6$)alkyl, ($C_2$-$C_6$)alkenyl, ($C_2$-$C_6$)alkynyl wherein the alkyl, alkenyl or alkynyl groups are optionally substituted by one to three halo in the presence of a lipase and an aqueous buffer solution; and (b) reacting the compound of formula IV so formed

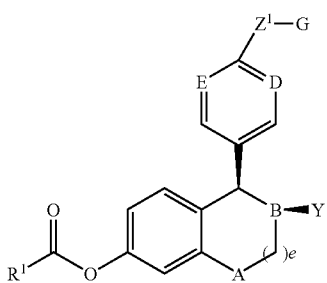

IV wherein $R^1$ is as defined above, with a base in the presence of a polar protic solvent.

2. A process according to claim 1, wherein the aqueous buffer solution is a phosphate, citric acid or boronic acid solution.

3. A process according to claim 1, wherein the lipase is from *Mucor miehel*.

4. A process according to claim 1, wherein the base is sodium methoxide, sodium hydroxide, lithium hydroxide or potassium hydroxide.

5. A process according to claim 1, wherein the polar protic solvent is methanol, ethanol or water.

6. A process according to claim 1, wherein the lipase is immobilized on a solid support.

7. A process according to claim 1, wherein the lipase is a cross-linked enzyme.

8. A process according to claim 1, wherein the lipase is in pure crystalline form.

9. A process according to claim 1, for preparing a compound of the formula

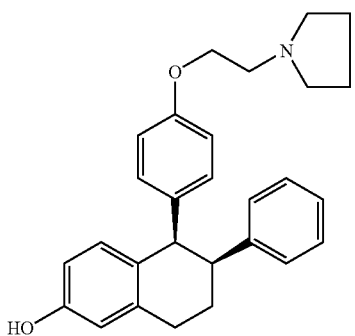

VII comprising enzymatically resolving of a compound of the formula

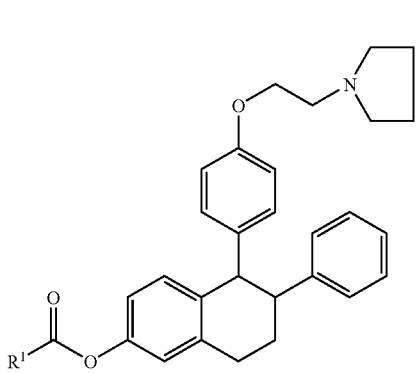

VIII wherein $R^1$ is $(C_1-C_6)$alkyl, $(C_2-C_6)$alkenyl, $(C_2-C_6)$alkynyl wherein the alkyl, alkenyl or alkynyl groups are optionally substituted by one to three halo in the presence of a lipase and an aqueous buffer solution; and (b) reacting the compound of Formula X so formed

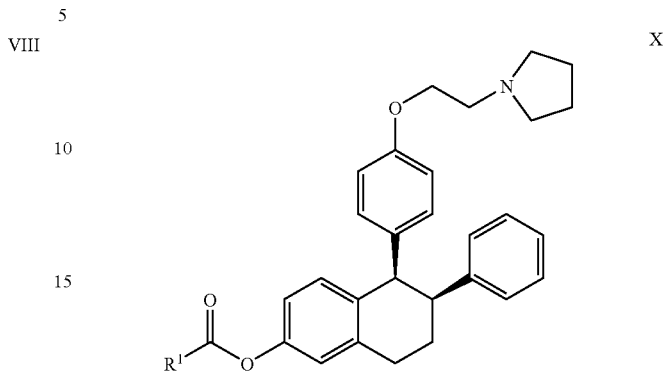

X wherein $R^1$ is as defined above, with a base in the presence of a polar protic solvent.

* * * * *